United States Patent [19]
Sellmer-Wilsberg et al.

[11] Patent Number: 5,979,219
[45] Date of Patent: Nov. 9, 1999

[54] PROBE FOR MEASURING VOLATILE COMPONENTS IN AN AQUEOUS SOLUTION

[75] Inventors: Sylvia Sellmer-Wilsberg, Rheinbreitbach, Germany; Hans-Werner Wilsberg, Haupstr. 95-97, 53619 Rheinbreitbach, Germany

[73] Assignees: Sylvia Sellmer Wilsberg; Hans-Werner Wilsberg, both of Rheinbreitbach, Germany

[21] Appl. No.: 09/016,303

[22] Filed: Jan. 30, 1998

[30] Foreign Application Priority Data

Feb. 3, 1997 [DE] Germany ............................ 197 03 744
Feb. 3, 1997 [DE] Germany ........................ 297 01 642 U

[51] Int. Cl.$^6$ ................................. G01N 7/12; G01N 1/22
[52] U.S. Cl. ........................ 73/19.12; 73/61.41; 73/64.56
[58] Field of Search .................................. 73/19.12, 19.1, 73/31.07, 61.44, 61.59, 64.56, 863.23

[56] References Cited

U.S. PATENT DOCUMENTS

| | | | |
|---|---|---|---|
| 4,550,590 | 11/1985 | Kesson .................................... | 73/19.12 |
| 4,745,796 | 5/1988 | Abdelrahman et al. ............... | 73/19.12 |
| 5,054,328 | 10/1991 | Long et al. ........................... | 73/864.81 |
| 5,144,831 | 9/1992 | Hale et al. ............................ | 73/19.05 |
| 5,255,553 | 10/1993 | Hale et al. ............................ | 73/19.1 |
| 5,331,845 | 7/1994 | Bals et al. ............................. | 73/61.43 |

FOREIGN PATENT DOCUMENTS

| | | |
|---|---|---|
| 0054537 | 2/1986 | European Pat. Off. . |
| 0174417 | 3/1988 | European Pat. Off. . |
| 3126648 | 7/1983 | Germany . |
| 3611596 | 4/1986 | Germany . |
| 19604606 | 2/1996 | Germany . |

OTHER PUBLICATIONS

Biotechnology Letters, vol. 5, pp. 509–514 (1983) On–Line Measurement of Ethanol with a Gas–Sensor–Dip–Electrode, Vorlop et al.

"On–Line Measurement Of Ethanol With A Gas–Sensor–Sip–Electrode", By K. D. Vorlop, et al Biotechnology Letters vol. 5 No. 8 509–514 (1983).

*Primary Examiner*—Michael Brock
*Attorney, Agent, or Firm*—Antonelli, Terry, Stout & Kraus, LLP

[57] ABSTRACT

The invention relates to a probe for measuring volatile components in an aqueous solution, for example to determine the alcohol concentration of an aqueous solution, with a probe body with a continuous lumen and a membrane disposed transversely with respect to the lumen, which isolates the lumen from the outside, and with a semiconductor gas sensor disposed in a housing inside the lumen at a distance from the membrane forming a measuring chamber filled with air, said sensor responding to the gases permeating the membrane by changing its electrical resistance, with an open continuous pressure relief channel being provided for the outflow of the gases permeating into the measuring chamber on the side of the sensor and the measuring chamber facing away from the membrane, and the pressure relief channel being connected at one end through an opening to the measuring chamber and at the other end on the outlet side having an outlet opening of a size such that the volume flow of the gas permeating through the membrane into the measuring chamber is always slightly larger than the volume flow of the gas leaving the measuring chamber through the outlet opening of the pressure relief channel.

11 Claims, 2 Drawing Sheets

PROBE FOR MEASURING VOLATILE COMPONENTS IN AN AQUEOUS SOLUTION

BACKGROUND OF THE INVENTION

The invention relates to a probe for measuring volatile components in an aqueous solution, for example to determine the alcohol concentration of an aqueous solution, with a probe body with a continuous lumen and a membrane disposed transversely with respect to the lumen, which isolates the lumen from the outside and with a semiconductor gas sensor disposed in a housing inside the lumen at a distance from the membrane forming a measuring chamber filled with air, said sensor responding to the gases permeating the membrane by changing its electrical resistance.

A probe for measuring organic solvents in a liquid using a semiconductor gas sensor in a closed measuring chamber with a liquid-impermeable membrane, through which the gases diffuse, is known from DE 31 26 648 C2. As the concentration of the measured components decreases, the gas enriched in the measuring chamber diffuses back through the membrane into the liquid. This probe however operates very slowly and is therefore unsuitable for use in industrial processes due to the very slow gas circulation by back-diffusion through the membrane.

Other probes for removal of volatile components from liquids or gases, for example to determine the concentration, and which operate with a permeation membrane as well as a sensor, are known for example from EP-A 0174 417 and EP-A 0054 537. In these known probes, permeation membranes based on a tubular silicone body are used, through which membranes the volatile components to be measured permeate at various rates depending on their concentrations and then reach the sensor, which, because of its electrical properties, changes its resistance according to the concentration of the components to be measured and emits corresponding measuring signals. To increase the measurement efficiency, the tubular permeation membrane is flushed with a carrier gas.

The disadvantage of these known probes is that, by using the tubular silicone membranes, which do not have substance-specific separating effects, not only is the desired substance/gas to be measured separated from the liquid and measured, but other gases and substances also distort the measurement result for a desired substance.

Moreover, the known silicone membranes have well-delimited diffusion rates, particularly with respect to alcohol, so that it becomes necessary to have a very large membrane surface area.

Thus, DE 196 04 606 A1 has already proposed a measuring device for one of at least two volatile components of a liquid, in which a permeation membrane composed of at least two layers with different permeation resistances and a carrier gas used in conjunction with a sensor.

SUMMARY OF THE INVENTION

The goal of the invention is to provide a probe for determining in particular volatile components in an aqueous solution, preferably the alcohol concentration of an aqueous solution, that makes possible higher measuring accuracy and a higher measuring rate and long-term problem-free use in industrial processes with continuous measurement without the use of a carrier gas.

This goal is achieved according to the invention with a probe according to the species, characterized in that an open continuous pressure relief channel is provided for the outflow of the gases permeating into the measuring chamber on the side of the sensor and the measuring chamber facing away from the membrane, and the pressure relief channel is connected at one end through an opening to the measuring chamber and at the other end on the outlet side has an outlet opening of a size such that the volume flow of the gas permeating through the membrane into the measuring chamber is always slightly larger than the volume flow of the gas leaving the measuring chamber through the outlet opening of the pressure relief channel.

According to the invention, by means of the pressure relief channel, the gases flow out from the measuring chamber directly into the atmosphere via the pressure relief channel, which is always open. It is thus possible to limit the partial pressure that is produced and develops in the measuring chamber due to the gases diffusing in through the membrane. Because of the gases, for example alcohol and ethanol, permeating into the measuring chamber from the liquid to be measured, the gas concentration, for example the alcohol concentration, rises proportionally in the measuring chamber so that measurement can be accurate and continuous. The outflow of gases permeating into the measuring chamber made possible by the invention to a lesser degree than the volume flow of the gas permeating into the measuring chamber makes it possible continuously to concentrate the alcohol in the measuring chamber proportionally to the alcohol concentration of the liquid to be measured. Surprisingly, it has been found that the ability of the probe to function and the measurement efficiency are considerably improved by discharging the gases from the measuring chamber through a separate pressure relief channel. A carrier gas is no longer needed to flush the membrane. The probe according to the invention can operate problem-free for a long period of time and can be used in industrial processes such as fermentation processes. Also, only a small membrane surface area is necessary. A further advantage of the probe according to the invention is that it does not have to be immersed in the liquid to be measured.

Advantageous embodiments of the invention appear in the characterizing features of the subclaims.

According to the invention, a membrane suitable for pervaporation is used to measure the alcohol concentration in an aqueous solution.

Pervaporation means a combination of evaporation and membrane permeation. In this case, it is a membrane separation technique in which one side of a pore-free polymer membrane—pervaporation membrane—is in contact with a liquid mixture of various components, while the permeate is removed in the vapor phase at the other side of the membrane. The flow through the membrane is caused by a partial pressure gradient across the membrane.

In addition to known membranes based on silicone and/or polytetrafluoroethylene, which have been successfully used for permeation of alcohols from alcohol/water mixtures, according to the invention multilayer membranes can also be used, and have a higher separation efficiency.

Pervaporation membranes produced on the basis of aromatic polyimides, polyamides, polyamidimides, polysulfones, polyvinyl chloride, polyacrylonitrile, polyacrylamides, polyetheretherketone, polyetherketone, polyethersulfone, or polyetherimide and having a selective layer based on polysiloxanes such as polydimethylsiloxane or polyoctamethylcyclotetrasiloxane with a selective layer thickness of 10–20 $\mu$m have proved to be suitable for a separation effect for ethanol.

The semiconductor gas sensors that can be used for the invention are commercially available, as described in the preambles of the European published applications referred to above. For example, semiconductor sensors made by Unitronic GmbH under number TGS 822 can be used for the invention.

The probe according to the invention is distinguished by a particularly simple design with an outer probe body with a continuous lumen and a second so-called inner body that can be inserted from one side into the lumen of the probe body. Preferably, both the probe body and the inner body are cylindrical or made as rotationally symmetric parts, as can be the lumen and bores. This makes it possible to construct the probe in a very simple manner by nesting, with the pervaporation membrane again being in the form of a flat disk and the lumen on the end of the probe body extending transversely inside the probe body forming a measuring chamber separated from the external atmosphere and environment, in which chamber the sensor and its housing are located. The housing of the sensor delimits the measuring chamber on the side opposite the membrane. Gases penetrating the pervaporation membrane pass through the measuring chamber to arrive at the sensor and, by changing the resistance of the latter, emit a signal that is conducted through measuring leads of an associated evaluation electronic circuit, for example with a microprocessor and display unit.

The outflow of the gases permeating into the measuring chamber is made possible by the pressure relief channel, which is preferably brought outward by the inner body of the sensor housing. At the same time the position of the sensor and/or its housing in the probe body can be determined with the aid of the inner body. The pressure relief channel is sealed off along its path through the probe at all transitions, for example from the housing of the sensor to the sensor plug or to the inner body, by sealing rings disposed therebetween.

The pressure relief channel can have a larger cross section than the outlet opening at the end thereof in order to form an air cushion.

For the purposes of simple design, assembly, and disassembly, and exact positioning and easy cleaning of the probe, it is proposed that the probe body have a threaded cap that can be mounted on and attached to the front end of the probe body, said cap having a central through-opening. This makes it possible to dispose the membrane on the front end of the probe body abutting it externally and to attach it by means of the threaded cap, possibly with interposition of a sealing ring.

In this way, the pervaporation membrane is attached between the end and the threaded cap while the sensor is inserted and secured inside the probe body in the lumen in a specific position. The gases are removed from the measuring chamber through the inner body, which is provided with a continuous channel and a specific outlet opening. The outlet opening of the pressure relief channel is always smaller than the inlet bore of the probe leading to the measuring chamber and covered by the membrane. Preferably, the outlet opening can be less than 10% of the size of this inlet bore. The volume flow of gas permeating into the measuring chamber is determined by the size of the effective membrane surface that comes in contact with the liquid to be measured and by the separation efficiency of the membrane, namely the materials of which the membrane is made. The size, i.e. the outlet cross section, of the outlet opening should be chosen such that the volume flow entering the atmosphere through the outlet opening is always kept smaller than the gas volume flow permeating into the measuring chamber to ensure that the alcohol or the gas to be measured is concentrated in the measuring chamber. In this way, the volume ratios in the measuring chamber are always defined, making possible accurate measurement of the alcohol concentration in an aqueous liquid by means of the alcohol permeating through the pervaporation membrane by means of the sensor. The outlet opening must be small enough to allow a sufficient partial pressure to develop due to inward diffusion of the gases through the membrane in the measuring chamber.

The structure of the probe body according to the invention with parts that are essentially rotationally symmetric makes it possible to manufacture them economically and assemble, disassemble, and clean the probe easily. Moreover, the positions of the membrane and sensor with respect to each other can be precisely determined so that the size of the measuring chamber can be defined and determined; likewise the effective membrane surface available for gas exchange by diffusion exposed by the inlet bore in the lumen of the probe body.

BRIEF DESCRIPTION OF THE DRAWINGS

The invention and its further design is described on the basis of embodiments in the drawing below.

DETAILED DESCRIPTION OF THE PREFERRED EMBODIMENTS

Figure 1:
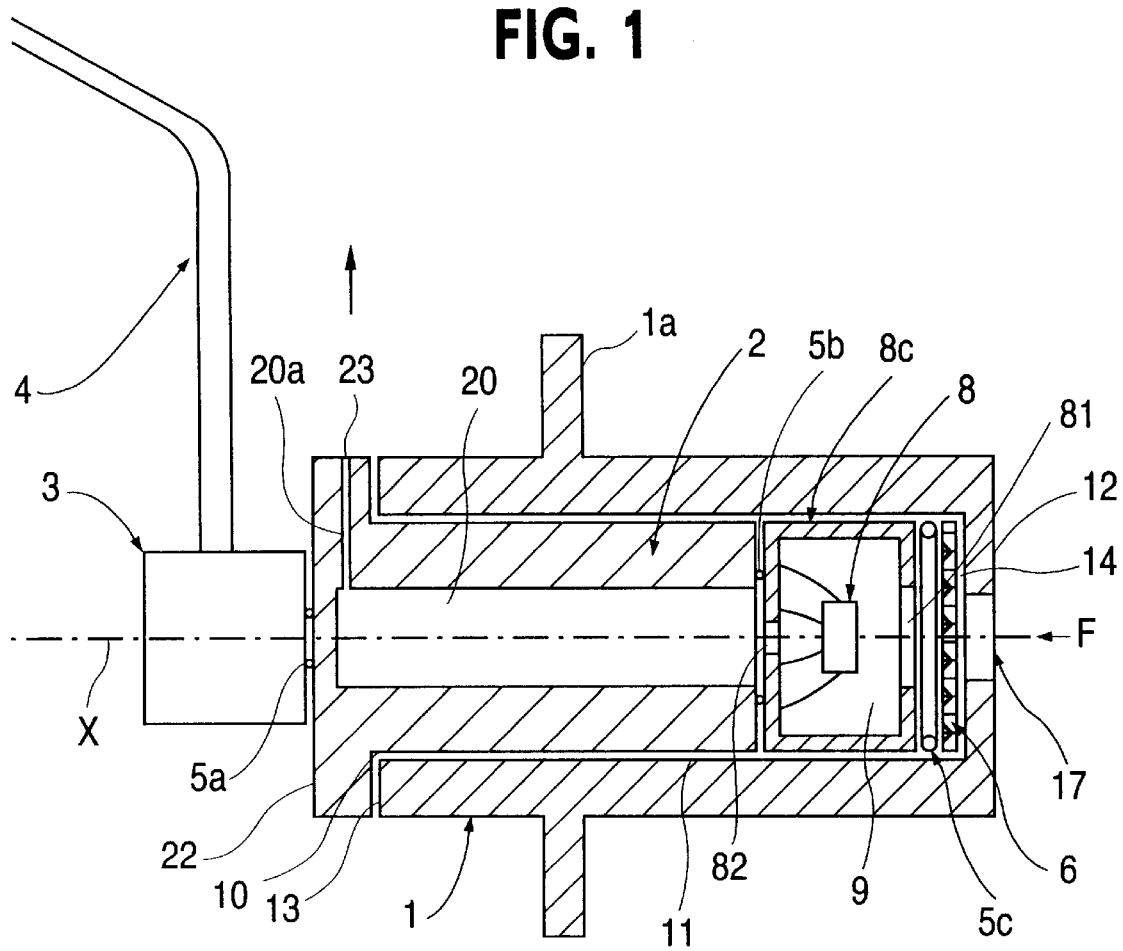
FIG. 1 shows a probe for measuring alcohol concentration with a one-piece outer probe body shown schematically in lengthwise section.

The probe according to FIG. 1 has a cylindrical tubular probe body 1 which is partially closed by a wall at its end 12, and has a central inlet bore 17 in the wall. The internal cavity of probe body 1 forms lumen 11, which runs from inlet bore 17 to the rear face 13 of the probe body. In the vicinity of end 12 of the probe body, a pervaporation membrane 6 in the shape of a flat disk is disposed transversely with respect to lumen 11 and transversely with respect to lengthwise axis X of probe body 1 inside probe body 1, so that lumen 11 is isolated from the outside by membrane 6. The membrane in this case abuts the inside of the wall of end 12 of probe body 1. Inlet bore 17 is covered by membrane 6 and the size of inlet bore 17 determines the effective membrane surface available for diffusion. The end of the probe is made to contact liquid F to be measured, which reaches membrane 6 through inlet bore 17.

Housing 8c with semiconductor gas sensor 8 located inside is disposed in lumen 11 with interposition of a sealing ring 5c. Housing 8c of the sensor has an inlet opening 81 on the side facing membrane 6 and an outlet opening 82 on the opposite side, said openings preferably being disposed coaxially to lengthwise axis X of the probe body. Semiconductor gas sensor 8 is disposed inside the housing and suspended therein. The electrical connections are brought to a plug 3 located at the rear end of inner body 2 at the rear end of the probe, the leads 4 of said plug leading to an evaluation unit and display unit. The TGS 822 sensor made by Unitronic GmbH referred to in the preamble hereof can for example be used as the semiconductor gas sensor.

Measuring chamber 9 filled with air is formed inside housing 8c of the sensor up to membrane 6. On the side of housing 8c of the sensor facing away from membrane 6 there abuts inner body 2 inserted into lumen 11 from rear end 13 of probe body 1, said body likewise being shaped as a cylindrical body and having a through-bore, said bore forming pressure relief channel 20 and abutting outlet opening 82 of housing 8c. In the vicinity of the rear end of the probe and/or inner body 2, the pressure relief channel has a small outlet opening 23 of a specific size, said opening being brought outward, for example as lateral bore 20a through inner body 2. Outlet opening 23 can also be brought out through plug 3. Outlet opening 23 must be made very small, and in particular must be substantially smaller than inlet bore 17, as it serves only to conduct the gases permeating into the measuring chamber into the atmosphere.

In the probe according to the invention, pervaporation membrane 6 is shaped like a flat disk which is combined with semiconductor gas sensor 8 in such a way that because of the disposition of membrane 6 in the shape of a flat disk at the end of cylindrical probe body 1 open on account of lumen 11, an air-filled space is separated inside the probe body from liquid F to be analyzed. This air-filled space is delimited by housing 8c of the sensor on the side facing away from the membrane and forms measuring chamber 9. The size of measuring chamber 9 is determined by the interior of sensor housing 8c and by the space 9a of lumen 11 still remaining between membrane 6 and the front side of the housing with inlet opening 81.

Semiconductor gas sensor 8 responds by changing its resistance, especially reducing its resistance due to the increase in gas or vapor concentration in the measuring chamber. The change in resistance triggers an electrical signal so that the changing alcohol concentration to be measured can be measured in measuring chamber 9 by the alcohol permeating through membrane 6 from liquid F.

Housing 8c with sensor 8 is accommodated in probe body 1, i.e. in lumen 11 thereof, in such fashion, and is positioned by the second inner body 2 inserted into probe body 1, that the housing, with its front side, with interposition of sealing ring 5c, presses membrane 6 against the front end on the inside on the probe body and holds it in place. The gas can flow out into the atmosphere from measuring chamber 9 only through the outlet bore 23 located at the rear end of inner body 2 via outlet opening 82 of the housing and pressure relief channel 20 of the inner body. This produces a gas mixture in measuring chamber 9, whose alcohol content is in a continuous diffusion equilibrium with liquid F to be measured. The alcohol concentration of the measuring chamber atmosphere bring about the change in resistance at the surface of gas sensor 8. This change in resistance can expressed as a mathematical relationship with the alcohol concentration, using suitable algorithms, i.e. the measuring signal is fed to a computer.

Figure 2:
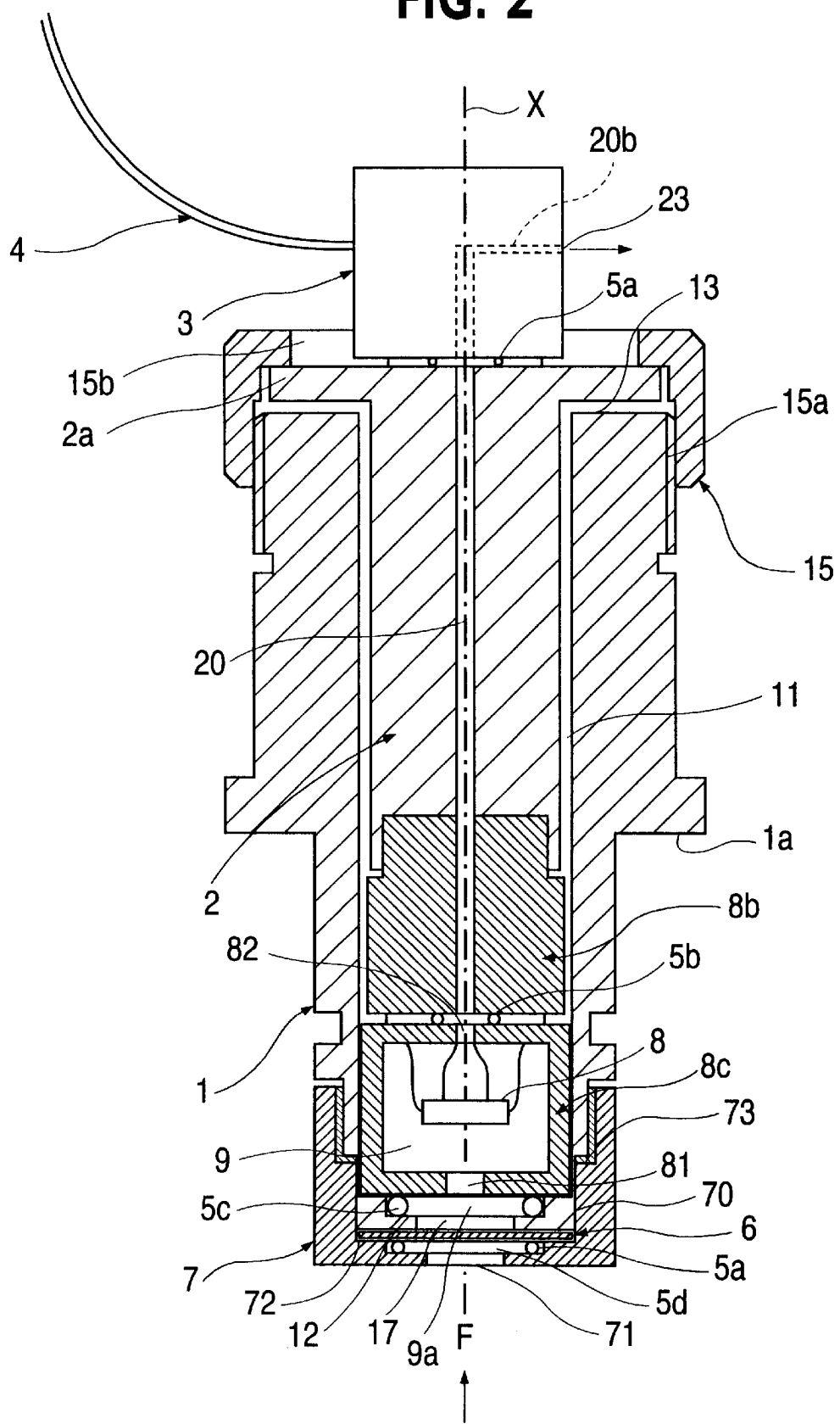
FIG. 2 shows a probe for measuring alcohol concentration with a multipartite design with a probe body in lengthwise section, shown schematically.

A modified form of the probe in FIG. 1 is shown in FIG. 2, where the probe has a multipartite design, with a threaded cap 7 being mounted at the front end 13 of probe body 1. Threaded cap 7 also has an inlet opening 71 in its head.

It is possible, with the aid of threaded cap 7, to apply membrane 6 to the front exterior of end 12 of the probe body as a flat disk and attach it by means of threaded cap 7 mounted thereof. Preferably another sealing ring 5d is inserted between the threaded cap and the membrane. This probe design makes it easy to clean or replace membrane 6. Liquid F to be measured can, in this case as well, contact membrane 6 directly through opening 71 in the direction of arrow P1, while the gases on the other side reach the measuring chamber through inlet bore 17 of the probe body.

Sensor 8 with its housing 8c is accommodated inside probe body 1 in the lumen; specifically it directly abuts the inside of end wall 12 of the probe body with interposition of a sealing ring 5c. Additionally, the sensor can be equipped with a sensor plug 8b on the rear side of its housing, said plug 8b also being connected with housing 8c with interposition of a sealing ring 5b. Inner body 2 abuts plug 8b, said body being inserted into the lumen from rear end 13 of the probe body, and determining the position of the sensor with housing 8c and plug 8b. Inner body 2 is for example formed at its rear end with a lateral flange 2a abutting the probe body endwise and attached to probe body 1 by means of screw cap 15 with screw thread 15a. The head of screw cap 15 has a through-opening 15b. Connecting plug 3 is mounted at the rear end of inner body 2, with leads 4 for electrical connection to sensor 8 which is inserted through opening 15b in the screw cap. Pressure relief channel 20, adjacent to outlet opening 82 of housing 8c of the sensor, is guided all the way through plug 8b of the sensor and inner body 2 as well as through plug 3 up to outlet opening 23. Pressure relief channel 20 is continuously open, i.e. outlet opening 23 is not closed. In this way, the gases to be measured can travel from liquid F by contacting membrane 6 into measuring chamber 9 and reach sensor 8, where they can be detected and the signals generated can then be passed on to the evaluation unit. Then the desired outflow of the gases permeating the measuring chamber into the atmosphere from measuring chamber 9 can then take place through pressure relief channel 20 brought out at the rear at the end of the probe.

Probe body 1 has a flanged projection 1a on the exterior, by which it can be placed in contact with a wall or the like. Pressure relief channel 20 is sealed off all the way through to the rear end at each transition with the elements aligned with one another by means of sealing rings 5b inserted therebetween, between sensor housing 8c and sensor plug 8b and/or inner body 2 and plug 3 by means of sealing ring 5a.

The probe according to FIG. 2 is characterized by a simple design using essentially rotationally symmetric parts which simply need to be connected together. The membrane is positioned and secured at the forward end of the probe body by means of the threaded cap while the sensor is positioned and secured to the housing by means of inner body 2 inserted into the lumen of the probe body. Pressure relief channel 20 is preferably guided in a central coaxial manner along lengthwise axis X of the probe, extending into plug 3 and provided therein with an outlet opening 23 by means of a lateral bore 20b.

The probe according to the invention permits high measurement accuracy with a sufficiently rapid method of operation and operates problem-free for a long period of time so that it can be used advantageously in industrial processes for monitoring production processes.

The probe according to the invention can be manufactured reproducibly regarding the size of the measuring chamber, the size of the effective membrane surface, and the volume of gases flowing out of the measuring chamber into the atmosphere through the outlet opening of the pressure relief channel, even during assembly and after disassembly, thus always providing reliable measurement.

We claim:

1. Probe for measuring volatile components in an aqueous solution, for example to determine the alcohol concentration of an aqueous solution with a probe body with a continuous lumen and a membrane disposed transversely with respect to the lumen at a front end of the lumen, which isolates the lumen from the outside, and with a semiconductor gas sensor disposed in a housing inside the lumen at a distance from the membrane forming a measuring chamber filled with air, said sensor responding to the gases permeating the membrane by changing its electrical resistance, characterized in that an inner body is provided on the side of the sensor or housing of the sensor facing away from the probe body from a rear end of probe body, with the inner body being in an operational connection with the housing of the sensor so that it secures the position of at least the housing with the sensor, and in that an open continuous pressure relief channel is brought through the inner body for the outflow of the gases permeating into the measuring chamber on the side of the sensor and the measuring chamber facing away from the membrane, and the pressure relief channel is connected at one end through an opening to the measuring chamber and at the other end on the outlet side has an outlet opening of a size such that the volume flow of the gas permeating through the membrane into the measuring chamber is always slightly larger than the volume flow of the gas leaving the measuring chamber through the outlet opening of the pressure relief channel.

2. Probe according to claim 1, characterized in that the probe body has an inlet bore that is smaller than the front end of the lumen at its front end by virtue of the formation of an end wall and the membrane is located so that it covers the inlet bore, wherein a cross section of the outlet opening of the pressure relief channel is smaller than the cross section of inlet bore.

3. Probe according to claim 1 characterized in that the probe body with the lumen is designed as a hollow cylinder and the inner body is designed as a cylindrical body with an axial continuous pressure relief channel.

4. Probe according to claim 1, characterized in that the probe body has a threaded cap which can be mounted on and secured to the front end of the probe body, said cap having a central through-opening the membrane being disposed abutting the outside of the front end of the probe body and being attached by means of the threaded cap.

5. Probe according to claim 1, characterized in that a screw cap with a screw thread and a through-opening through a head of the screw cap is provided on the rear end of the probe body to attach the inner body to the probe body.

6. Probe according to claim 1, characterized in that a plug for electrical connection with the sensor is disposed at the rear end of the inner body, and the pressure relief channel is continued from the inner body through the plug up to the outlet opening.

7. Probe according to claim 1, characterized in that a sealing ring (5a) surrounding pressure relief channel (20) is provided between the rear end of inner body (2) and mounted plug (3).

8. Probe according to claim 1, characterized in that, between the housing (8c) of the sensor and the inner body and/or a sensor plug abutting housing of the sensor, a sealing ring surrounding the pressure relief channel is disposed.

9. Probe according to claim 1, characterized in that housing (8c) of the sensor has an inlet opening (81) on the side facing membrane (6), said opening being made symmetrical to the lengthwise axis (X) of the cylindrical probe body as well as the inlet bore (17) or probe body (1) and pressure relief channel (20).

10. Probe according to claim 1, characterized in that the membrane is a multilayer pervaporation membrane, whose substance-specific separating effect is designed for ethanol.

11. Probe according to claim 1, characterized in that the cross section of the pressure relief channel is larger than the cross section of the outlet opening.

* * * * *